(12) United States Patent
Haridas (10) Patent No.: US 7,492,462 B2
(45) Date of Patent: *Feb. 17, 2009

(54) OPTOCHEMICAL SENSOR

(75) Inventor: Manoj Haridas, Bangalore (IN)

(73) Assignee: Honeywell International, Inc., Morristown, NJ (US)

( * ) Notice: Subject to any disclaimer, the term of this patent is extended or adjusted under 35 U.S.C. 154(b) by 264 days.

This patent is subject to a terminal disclaimer.

(21) Appl. No.: 11/332,398

(22) Filed: Jan. 17, 2006

(65) Prior Publication Data

US 2007/0165236 A1    Jul. 19, 2007

(51) Int. Cl.
  *G01B 9/02* (2006.01)
  *G01J 3/44* (2006.01)
  *G01N 21/00* (2006.01)
(52) U.S. Cl. .................. 356/456; 356/73; 356/301
(58) Field of Classification Search ........ 356/451, 356/453, 301, 73, 456; 250/339.07, 339.09
See application file for complete search history.

(56) References Cited

U.S. PATENT DOCUMENTS

| 3,782,828 | A | * | 1/1974 | Alfano et al. | 356/318 |
|---|---|---|---|---|---|
| 3,973,849 | A | * | 8/1976 | Jackson et al. | 356/320 |
| 4,620,284 | A | * | 10/1986 | Schnell et al. | 702/28 |
| 5,112,127 | A | * | 5/1992 | Carrabba et al. | 356/301 |
| 5,255,067 | A | * | 10/1993 | Carrabba et al. | 356/301 |
| 5,483,546 | A | * | 1/1996 | Johnson et al. | 372/10 |
| 5,689,333 | A | * | 11/1997 | Batchelder et al. | 356/301 |
| 5,784,158 | A | * | 7/1998 | Stanco et al. | 356/326 |
| 5,828,450 | A | * | 10/1998 | Dou et al. | 356/301 |
| 6,351,307 | B1 | * | 2/2002 | Erskine | 356/451 |
| 6,717,668 | B2 | * | 4/2004 | Treado et al. | 356/327 |
| 7,092,101 | B2 | * | 8/2006 | Brady et al. | 356/456 |
| 7,177,496 | B1 | * | 2/2007 | Polynkin et al. | 385/24 |
| 7,283,232 | B2 | * | 10/2007 | Brady et al. | 356/326 |
| 7,301,624 | B2 | * | 11/2007 | Talley et al. | 356/301 |
| 7,355,705 | B1 | * | 4/2008 | Cohen et al. | 356/326 |
| 7,361,501 | B2 | * | 4/2008 | Koo et al. | 435/287.2 |
| 2004/0201850 | A1 | * | 10/2004 | Hajian et al. | 356/451 |
| 2007/0076208 | A1 | * | 4/2007 | Koo | 356/451 |

* cited by examiner

*Primary Examiner*—Patrick J Connolly
*Assistant Examiner*—Scott M Richey
(74) *Attorney, Agent, or Firm*—Darby & Darby, P.C.

(57) ABSTRACT

A sensor containing a beam emitter that emits a first beam having laser, a beam-splitting interferometer and an array detector, wherein the first beam is to strike a sample that produces a second beam comprising a Raman signal, the beam-splitting interferometer is to create a phase delay in the second beam, and the array detector comprises a plurality of detectors is disclosed. The sensor could be used for spectroscopic detection of a sample by generating a first beam comprising laser, striking the first beam to a sample to produce a second beam comprising a Raman signal, creating a phase delay in the second beam and detecting the Raman signal of the second beam. The uses of the sensor include detection of biological and chemical warfare agents, narcotics, among others for homeland security.

18 Claims, 7 Drawing Sheets

OPTOCHEMICAL SENSOR

RELATED APPLICATIONS

This application is related to U.S. patent applications having Ser. Nos. 11/332,162, 11/332,234, and 11/332,264, filed herewith along with this application, and incorporated herein by reference.

FIELD OF INVENTION

The embodiments of the invention relate to an interferometry Raman lidar-based sensor to analyze molecules and nanomaterials using optical signals from electromagnetic radiation including visible light, and it relates to methods and apparatus for preparing such sensors. The invention transcends several scientific disciplines such as analytical and molecular chemistry, optics, materials science, and medical or chemical diagnostics.

BACKGROUND

Remote molecular recognition of chemical species is desirable for forensic and surveillance of objects and persons, for example, at security checkpoints such as those at the airports. Thus, developing a better understanding of detecting chemical species is desired.

Chemical examination of approaching objects (and persons) needs to be done as much in advance as possible, and as accurately as possible. Chemical intelligence on a subject could be used for forensic, surveillance and military applications. While infrared (IR) sensors are widely used for chemical analysis, substances stored in containers and also materials such as $H_2O$ and $CO_2$ are difficult to analyze using IR sensors. The sensor of the embodiments of this invention overcomes these disadvantages of IR sensors. Also, the sensor of the embodiments of this invention can distinguish between allotropes, some of which may be explosives.

SUMMARY OF THE INVENTION

The embodiments of the invention relate to a sensor comprising a beam emitter that emits a first beam comprising laser, a beam-splitting interferometer, a spectrometer and an array detector, wherein the first beam is to strike a sample that produces a second beam comprising a Raman signal, the beam-splitting interferometer is to create a phase delay in the second beam, and the array detector comprises a plurality of detectors. The sensor could further comprise an edge filter and optical elements to collect the second beam and concentrate the second beam. In one variation, the spectrometer comprises diffraction gratings. The sensor could further comprise a microprocessor, wherein the microprocessor contains a library of Raman spectra. Furthermore, in one variation, the detector could be an array detector. Preferably, the detector is a charge coupled device, a transducer or a photodiode. The sensor could further comprise a sample collection device. In one variation, the interferometer could comprise an optical bench, a wafer having optical structures, an optical splitter or an optical waveguide. Preferably, the optical splitter or the optical waveguide comprises optical fibers coupled to each other to form the optical splitter or the optical guide.

Other embodiments of the invention relate to a method for spectroscopic detection of a sample, comprising generating a first beam comprising laser, striking the first beam to a sample to produce a second beam comprising a Raman signal, creating a phase delay in the second beam, passing the second beam through a spectrometer and detecting the Raman signal of the second beam. The method could comprise permitting transmission of the Raman signal of the second beam through a filtering device that substantially rejects non-Raman signals of the second beam. Preferably, the second beam is modified to substantially exclude all IR signals and include substantially only the Raman signal. The method could further comprise spreading the Raman signal onto a detector by the spectrometer. Preferably, the detector has a sensitivity to resolve overlapping Raman signals having a Raman scattering cross-section as low as about $10^{-29}$ $cm^2$/molecule. The method could further comprise analyzing an output of the detector. The method could still further comprise comparing Raman spectra stored in a library to a Raman spectrum from an output of the detector. The method could further comprise collecting the sample in a sample collection device.

Yet, other embodiments of the invention relates to a method of manufacturing a sensor, comprising locating (a) a beam emitter that emits a first beam comprising laser, (b) a beam-splitting interferometer, (c) a spectrometer and (d) a detector within the sensor in a manner such that the first beam strikes a sample and produces a second beam comprising a Raman signal, and the beam-splitting interferometer creates a phase delay in the second beam.

As will be realized, this invention is capable of other and different embodiments, and its details are capable of modifications in various obvious respects, all without departing from this invention. Accordingly, the drawings and description are to be regarded as illustrative in nature and not as restrictive.

DETAILED DESCRIPTION

As used in the specification and claims, the singular forms "a", "an" and "the" include plural references unless the context clearly dictates otherwise. The meaning of reference letters in the figures are as follows: LBE means laser mean emitter, LRF means laser range finder, EF means edge filter, I means interferometer, D means detector, S means spectrometer and QVP means quartz view port, SC means sample collector, M means microprocessor, OS means optical splitter, OB means optical bench, OSW means optical structures on a wafer, OW means optical waveguide, and OF means optical fiber.

In the embodiments of this invention, chemical species are detected remotely by Raman lidar-based sensor using optical signals from electromagnetic radiation including visible light. The sensors of the embodiments of the invention capture Raman signals from a sample resulting from Raman scattering from the sample.

Raman scattering is a powerful light scattering technique used to diagnose the internal structure of molecules and crystals. In a light scattering experiment, light of a known frequency and polarization is scattered from a sample. The scattered light is then evaluated for frequency and polarization.

Raman scattered light is frequency-shifted with respect to the excitation frequency, but the magnitude of the shift is independent of the excitation frequency. This "Raman shift" is therefore an intrinsic property of the sample.

Because Raman scattered light changes in frequency, the rule of conservation of energy dictates that some energy is deposited in the sample. A definite Raman shift corresponds to excitation energy of the sample (such as the energy of a free vibration of a molecule). In general, only some excitations of a given sample are "Raman active," that is, only some may take part in the Raman scattering process. Hence the frequency spectrum of the Raman scattered light maps out part of the excitation spectrum. Other spectroscopic techniques, such as IR absorption, could be used to map out the non-Raman active excitations.

Additional information, related to the spatial form of the excitation, derives from the polarization dependence of the Raman scattered light. The shape of an excitation in a material, for example a vibration pattern of the atoms in a molecule, and the polarization dependence of the scattering, are determined by the equilibrium structure of the material through the rules of group theory. By this route one gleans valuable and unambiguous structural information from the Raman polarization dependence.

Raman spectroscopy technique of the embodiments of the invention is based upon the Raman effect which may be described as the scattering of light from a gas, liquid or solid with a shift in wavelength from that of the usually monochromatic incident radiation.

Raman spectroscopy provides information about molecular vibrations that can be used for sample identification and quantification. The technique of the embodiments of the invention involves shining a monochromatic light (i.e., laser) on a sample. Laser-produced, monochromatic light of ultraviolet, visible, or infrared frequency could be used as the light source. In some embodiments of the Raman spectroscopy technique of the embodiments of the invention, visible lasers could used (e.g., Ar+, Kr+, Nd:YAG, He—Ne, diode) to create molecular vibration to high-energy "virtual" states of excitation. The laser sources could include among others: (1) Lexel 3000 Ar/ion (single line output, tuneable) having 514 nm, 502 nm, 496 nm, 488 nm, 477 nm, 473 nm, 466 nm, 458 nm, and 455 nm lines; (2) Uniphase 17 mW He—Ne at 633 nm; (3) Spectra Physics 125 He—Ne at 633 nm @45 mW, and 611 nm; tuneable; (4) Coherent 750 nm diode laser (45 mW max); and (5) Coherent Kr/ion (single line output, tuneable).

The light interacts with the sample and part of it is transmitted, part of it is reflected, and part of it is scattered. The scattered light is detected by one or more detectors. The majority of the scattered light is of the same frequency as the excitation source; this is known as Rayleigh or elastic scattering. A very small amount of the scattered light (less than 1%, but more likely about $10^{-5}$ of the incident light intensity), called Raman or inelastic scattering, has frequencies different from that of the incident light due to interactions between the incident electromagnetic waves and the vibrational energy levels of the molecules in the sample.

That is, the scattered radiation is examined spectroscopically, not only is light of the exciting frequency, $v_0$, observed (Rayleigh scattering), but also some weaker bands of shifted frequency are detected. Moreover, while most of the shifted bands are of lower frequency $v_0 - v_i$, there are some at higher frequency, $\|_0 + v_i$. By analogy to fluorescence spectrometry, the former are called Stokes bands and the latter anti-Stokes bands. The Stokes and anti-Stokes bands are equally displaced about the Rayleigh band; however, the intensity of the anti-Stokes bands is much weaker than the Stokes bands and they are seldom observed. The scattered radiation produced by the Raman effect contains information about the energies of molecular vibrations and rotations, and these depend on the particular atoms or ions that comprise the molecule, the chemical bonds connect them, the symmetry of their molecule structure, and the physico-chemical environment where they reside.

Plotting the intensity of this "shifted" light versus frequency results in a Raman spectrum of the sample. The Raman spectra could also be plotted as intensity versus the difference in frequency of the incident light and scattered light such that the Rayleigh band lies at $0\,cm^{-1}$ and the Raman band lie on both sides of the Rayleigh band. On this scale, the band positions could lie at frequencies that correspond to the energy levels of different functional group vibrations. The Raman spectrum can thus be interpreted similar to the infrared absorption spectrum.

The vibrational Raman effect is especially useful in studying the structure of the polyatomic molecule. If such a molecule contains N atoms it can be shown that there could be 3N-6 fundamental vibrational modes of motion only (3N-5 if the molecule is a linear one). Those which are accompanied by a change in electric moment can be observed experimentally in the infrared. The remaining ones, if occurring with a change in polarizability, could be observable in the Raman effect. Thus both kinds of spectroscopic measurements could be applied in a complete study of a given molecule.

Like infrared spectrometry, Raman spectrometry is a method of determining modes of molecular motion, especially the vibrations, and their use in analysis is based on the specificity of these vibrations. The methods are predominantly applicable to the qualitative and quantitative analysis of covalently bonded molecules rather than to ionic structures. Nevertheless, they can give information about the lattice structure of ionic molecules in the crystalline state and about the internal covalent structure of complex ions and the ligand structure of coordination compounds both in the solid state and in solution.

Both the Raman and the infrared spectrum yield certain description of the internal vibrational motion of the molecule in terms of the normal vibrations of the constituent atoms. However, IR absorption and Raman scattering are governed by completely different selection rules. Infrared bands arise from an interaction between light and the oscillating dipole moment of a vibrating molecule. Raman bands arise from an oscillation induced dipole caused by light waves interacting with the polarizability ellipsoid of a vibrating molecule. (It is common to describe the polarizability ellipsoid as the shape of the electron cloud around the molecule). Thus, symmetric stretches, vibrations involving multiple bonds, and vibrations of heavier atoms typically give rise to strong bands in the Raman spectrum. Asymmetric molecules could have bands at similar frequencies in both the infrared and Raman spectra, but their relative intensities could be very different. In most cases, a chemical species could have strong, indicative bands in both its Raman and IR spectra but they may not coincide.

Neither Raman nor IR spectra alone might give a complete description of the pattern of molecular vibration, and, by analysis of the difference between the Raman and the infrared spectrum, additional information about the molecular structure can sometimes be inferred. Physical chemists have made extremely effective use of such comparisons in the elucidation of the finer structural details of small symmetrical molecules, such as methane and benzene, but the mathematical techniques of vibrational analysis are not yet sufficiently developed to permit the extension of these differential studies to the Raman and infrared spectra of the more complex molecules that constitute the main body of both organic and inorganic chemistry.

Raman spectra are very specific, and chemical identifications can be performed by using search algorithms against digital databases. As in infrared spectroscopy, band areas are proportional to concentration, making Raman amenable to quantitative analysis. In fact, because Raman bands are inherently sharper than their infrared counterparts, isolated bands are often present in the spectrum for more straightforward quantitative analysis. By the technique of the embodiments of the invention, one can use Raman alone, or in combination with IR spectra, in two ways. At the purely empirical level they provide "fingerprints" of the molecular structure and, as such, permit the qualitative analysis of individual compounds, either by direct comparison of the spectra of the known and unknown materials run consecutively, or by comparison of the spectrum of the unknown compound with catalogs of reference spectra. By comparisons among the spectra of large numbers of compounds of known structure, it has been possible to recognize, at specific positions in the spectrum, bands which can be identified as "characteristic group frequencies" associated with the presence of localized units of molecular structure in the molecule, such as methyl, carbonyl, or hydroxyl groups. Many of these group frequencies differ in the Raman and infrared spectra.

Thus, by the Raman spectroscopy technique of the embodiments of the invention, wavelengths and intensities of the scattered light can be used to identify functional groups of molecules because each compound has its own unique Raman spectrum which can be used as a finger print for identification. It has found wide application in the chemical, polymer, semiconductor, and pharmaceutical industries because of its high information content.

Raman spectra, not only provides a chemical fingerprint, but also provides additional information including:

Identification of minerals and organic substances. From the identities of minerals, we know the chemical formulas and the arrangements of the atoms within them. Thus, we know whether the mineral was a carbonate, sulfate, phosphate, silicate, oxide, sulfide, hydroxide, etc. In some cases for which chemical compositions can vary, e.g., in the ratio of iron to magnesium ions, we can determine the cation ratio Easy sampling of solids, powders, gels, liquids, slurries, and aqueous solutions No sample preparation Sampling through windows, transparent containers, blister packs, or by immersion Remote sampling using fiber optic probes (up to 100 meters)

Sharp spectral peaks for quantitative and qualitative analysis

Identification of phases (mineral inclusions, daughter minerals in fluid inclusions, composition of the gas phase in inclusions)

Anions in the fluid phase ($CO_3^{2-}$, $HCO_3^-$, $PO_4^{3-}$, $BO_4^{3-}$, $SO_4^{2-}$, $HS^-$, $OH^-$)

Identification of crystalline polymorphs (sillimanite, kyanite, andalusite and others)

Measurement of mid-range order in solids

Measurement of orientation

Measurement of stress

High-pressure and high-temperature in situ studies

Phase transition and order-disorder transitions in minerals ($\alpha$-$\beta$ phase transition in quartz, graphite)

Water content of silicate glasses and minerals

Speciation of water in glasses

One embodiment of the invention relates to in-situ on-site Raman spectroscopy. This means analysis of the sample in its original location, which could be in a particular case at a security checkpoint at an airport. Usually, the analysis is done without any preparation of the sample such as cleaning. For chemicals used for explosives, for example, that means characterizing their properties as they are found within packed explosives. Through in-situ Raman spectroscopy, one can obtain the identities and characteristics of individual chemical species contained within an explosive.

Raman scattering technique of the embodiments of the invention is a spectroscopic technique that is complementary to infrared absorption spectroscopy. Raman offers several advantages over mid-IR and near-IR spectroscopy, including:

Little or no sample preparation is required

Water is a weak scatterer—no special accessories are needed for measuring aqueous solutions Water and $CO_2$ vapors are very weak scatterers—purging is unnecessary Inexpensive glass sample holders are ideal in most cases Fiber optics (up to 100's of meters in length) can be used for remote analyses Since fundamental modes are measured, Raman bands can be easily related to chemical structure Raman spectra are "cleaner" than mid-IR spectra—Raman bands are narrower, and overtone and combination bands are generally weak The standard spectral range reaches well below 400 $cm^{-1}$, making the technique ideal for both organic and inorganic species Raman spectroscopy can be used to measure bands of symmetric linkages which are weak in an infrared spectrum (e.g. —S—S—, —C—S—, —C=C—)

Raman scattering is, as a rule, much weaker than Rayleigh scattering (in which there is no frequency shift) because the interactions which produce Raman scattering are higher order. Therefore, it is preferred to use an intense source which is as monochromatic as possible—a laser with a narrow linewidth is usually used—and the collected light should be carefully filtered to avoid the potentially overwhelming Rayleigh signal. Other potentially large sources of non-Raman signal include fluorescence (the decay of long-lived electronic excitations) and of course light from ambient sources. Fluorescence can be particularly pernicious to a Raman measurement because the fluorescence signal is also shifted from the laser frequency, and so can be much more difficult to avoid. Note that although the fluorescence spectrum is shifted from the laser frequency, the fluorescence shift depends on the laser frequency whereas the Raman shift does not.

In one embodiment of the sensor of the invention, a laser beam, e.g., an Argon-ion laser, is filtered for monochromaticity and directed by a system of mirrors to a focusing/collecting lens. The beam is focused onto the sample and the scattered light from the sample is allowed to passes through a set of lens into a first stage of the spectrometer. Preferably, the sample should be oriented such that the specular reflection from the sample passes outside of the collection lens—otherwise, the laser signal could potentially damage the detector which is sensitive enough to see the weak Raman signal.

The spectrometer could be separated into two stages. The first stage is called a monochromator, but could be used as a filter, comprising two diffraction gratings, separated by a slit, with input and output focusing mirrors. The incoming signal from the collecting lenses could be focused on the first grating, which separates the different wavelengths. This spread-out light is then passed through a slit. Because light of different wavelengths is now traveling in different directions, the slit width can be tuned to reject wavelengths outside of a user-defined range. This rejection is often used to eliminate the light at the laser frequency, for example. The light which passes through the slit is then refocused on the second grating, whose purpose could be to compensate for any wavelength-dependence in the dispersion of the first grating. This grating could be oriented such that its dispersion pattern is the mirror image of that from the first grating. Finally the light could be refocused and sent out to the second stage.

The second stage focuses the filtered light on the final grating. The dispersed light is now evaluated as a function of position, which corresponds to wavelength. The signal as a function of position is read by the system detector. The detector could be a multichannel charge-coupled device array (CCD) in which the different positions (wavelengths) are read simultaneously. The wavelength/intensity information could then be read to a computer and converted to a frequency/intensity spectrum, which is the Raman data for the Raman spectrum.

The Raman data comes out as an intensity/frequency plot. To resolve a Raman peak of a certain width, the resolution of the spectrometer could be smaller than the peak width. In an embodiment of the invention, the resolution could be determined by a final slit between the third grating and the CCD array. The final dispersed image of the sample spot could be focused in the plane of the CCD array and the slit width could determine the extent to which the image may shift along the face of the CCD array, and hence the frequency resolution. When the sensor of the embodiments of the invention is properly aligned, the intensity could be a function of four factors: the applied laser power, the sample properties (how absorptive/reflective the sample is, and the intrinsic strength of the Raman modes), the width of the spectrometer's admission slit, and the width of the resolution slit.

By the sensor of the embodiments of the invention, preferably the first stage of the spectrometer filters out the laser frequency, while leaving the rest of the frequencies unaffected, and the second stage spreads the filtered light onto the CCD array, which could then respond uniformly to each frequency.

As the spectrometer in its parts or as a whole could have a wavelength (or frequency) dependent transmittance, the actual spectrum displayed is a product of the spectrometer frequency response with the actual spectrum of the scattered light. Thus, to know not only the energies of the Raman-active excitations, but also the relative magnitudes of the scattering at different frequencies, it is desirable to calibrate the spectrometer response to a source with a known spectrum. Thus, one could use a traceable standard lamp or a spectrum from a well-characterized piece of luminescent glass.

The light source of the embodiments of the invention includes lidar, which is like Radar, but uses light waves to bounce off a suspect specimen instead of radio waves. The preferred wavelengths for maximum signal-to-noise ratio (SNR) are 248, 266 and 355 nm to operate in the solar-blind region. However, lidar needs a transparent container such as glass or clear plastic bottle or a transparent port in the container holding the chemical species.

The embodiments of the sensor of this invention could be directed, for example by passing through a filter such as an optical filter, to substantially exclude IR signals and include substantially only Raman signals that are detected by a detector. The detection of a particular chemical species by the detector could be done by calibrating the detector.

In the embodiments of the sensor, the Raman signal intensity could be very low, i.e., the Raman scattering cross-section could be about $10^{-29}$ cm$^2$/molecule. Yet, the intensity would not depend on the wavelength of the light striking the sample. Instead, the Raman output signals of the embodiments of this invention would have a shift in wavelength with respect to the wavelength of the probing light (i.e. Raman shift).

Figure 1:
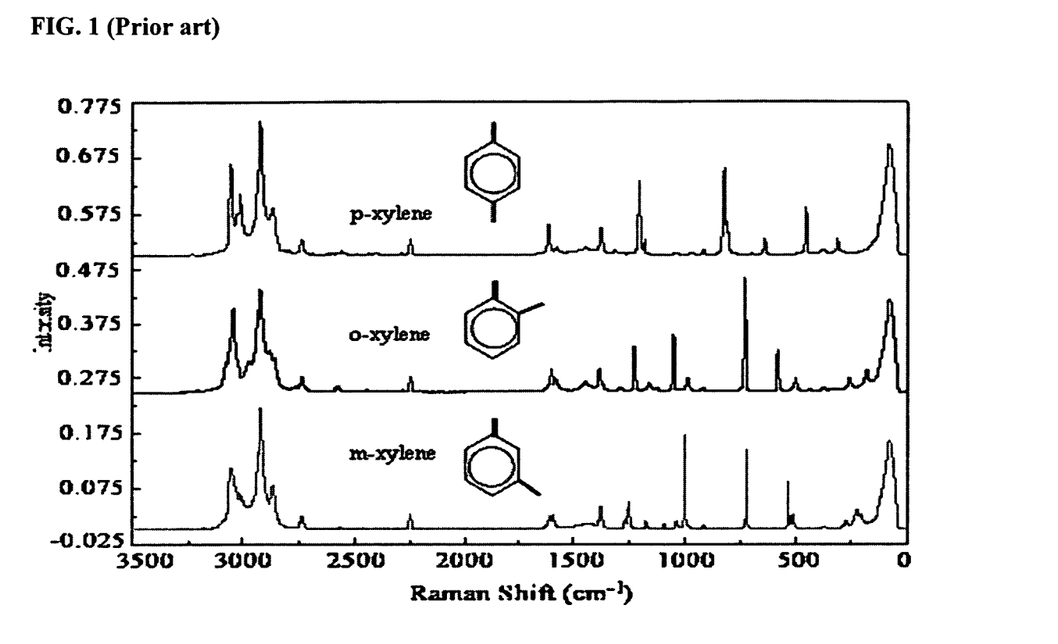
FIG. 1 shows representative Raman signals to distinguish chemical variants having a common structural backbone.

Raman spectroscopy also has the ability to distinguish chemical variants around a common structural backbone as shown by the Raman spectra of p-xylene, o-xylene and m-xylene in FIG. 1. Based on this capability, it would be possible the sensor of the embodiments of the invention to distinguish a harmful allotrope that might be disguised within a nonharmful allotrope, for example In one embodiment of the sensor of the invention, the requirements from a typical stand-off sensor could be the following:
(1) Analysis of a chemical species from a distance of greater than 30 meters.
(2) Sensitivity in ppb of the chemical species.
(3) Analysis of the chemical species should be completed within 200 seconds.

The applicant recognized that the prior art sensors do not meet these requirements for the following reasons:
(1) There is Raman cross-talk resulting from overlapping Raman bands. This in turn causes disguising species to hide a species of interest, which could be a harmful species.
(2) It takes a very long time to do the analysis due to the use of a single detector rather than an array of detectors.

Figure 2:
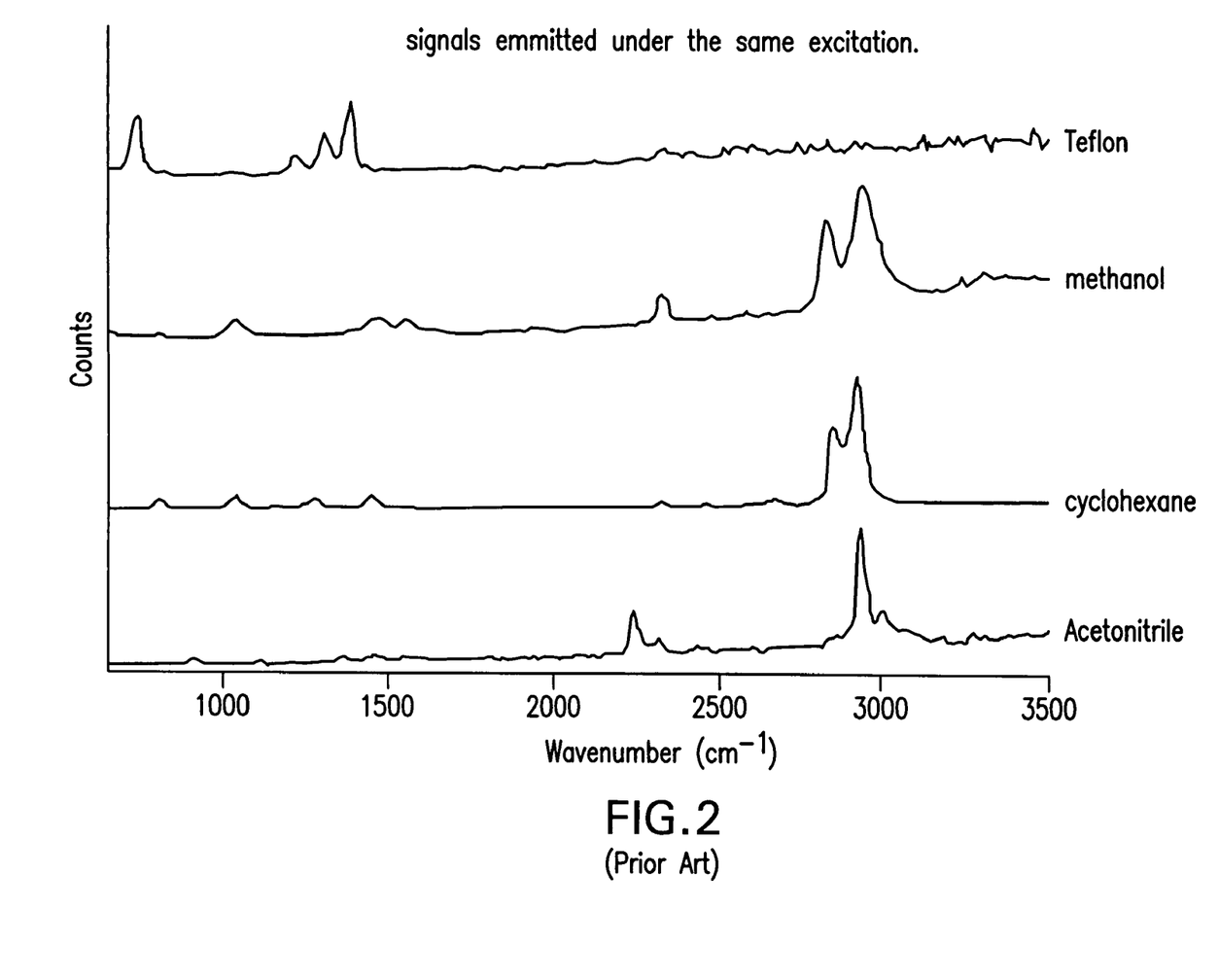
FIG. 2 shows representative Raman signals showing where different chemical variants have overlapping Raman peaks.

To better understand the Raman cross-talk effect from overlapping Raman bands, refer to FIG. 2 which shows representative results of a Raman analysis from Teflon, methanol, cylcohexane and acetonitrile. Even though the four materials have their own distinctive spectrum, one would notice that methanol, cyclohexane and acetonitrile all have peaks in their spectra at a wavenumber of about 3000 cm$^{-1}$. Suppose a sample contained methanol, cylcohexane and acetonitrile. Then, the composite spectrum arising from the combination of the individual spectra would have multiple peaks around wavenumber of about 3000 cm$^{-1}$ and it is possible that the peak from acetonitrile could be concealed behind the broader peaks of cyclohexane or methanol.

In light of this recognition, the applicant arrived at the embodiments of the sensor of this invention having the following features:
(1) Multiplexed arrays of Raman detectors allowing for parallel detection of Raman signals by several Raman detectors.
(2) Multiple arrays of analyzers—which could be either in the form of hardware or software, or a single high speed analyzer.
(3) Use of a beam-splitting interferometer to phase separates the signals from the disguising and harmful species using principles of interferometry, particularly, using Mach-Zehnder or Jamin interferometers (or any other interferometer suited for phase shift of signals from a Raman signature).
(4) UV Raman Lidar.
(5) CPU for directing signal traffic between the detectors and the analyzer(s) and also for controlling the operating of the different components of the sensor.

The unique functional properties of the embodiments of the sensor of the invention are:
(1) High detector sensitivity to resolve overlapping Raman signals having a Raman scattering cross-section as low as about $10^{-29}$ cm$^2$/molecule.
(2) Ability to magnify low SNR by lowering the optical noise by the beam-splitting interferometer (by making every photon count).

Figure 3A:
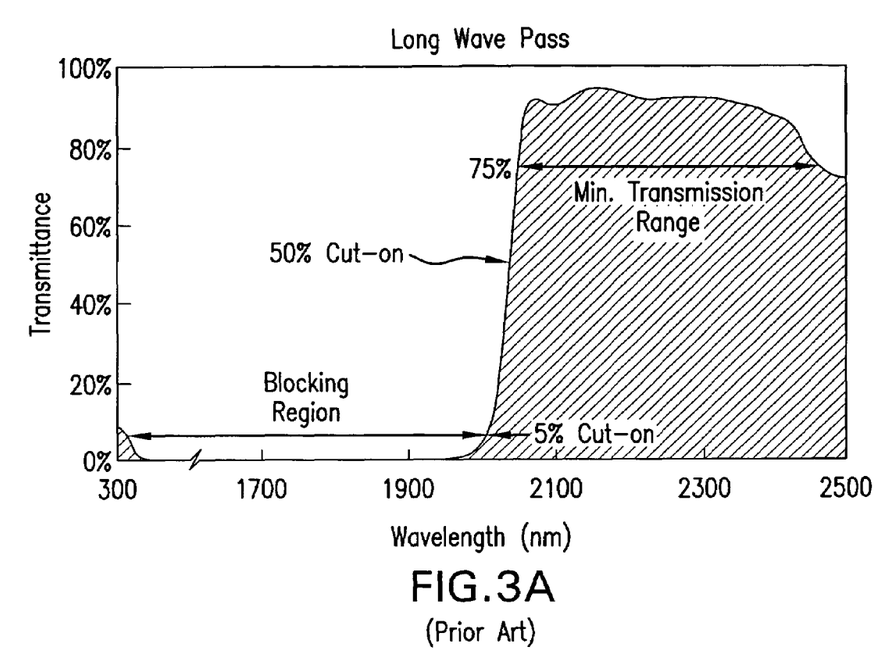
FIG. 3 shows transmittance spectrum of long and short wave pass edge filters.
Figure 3B:
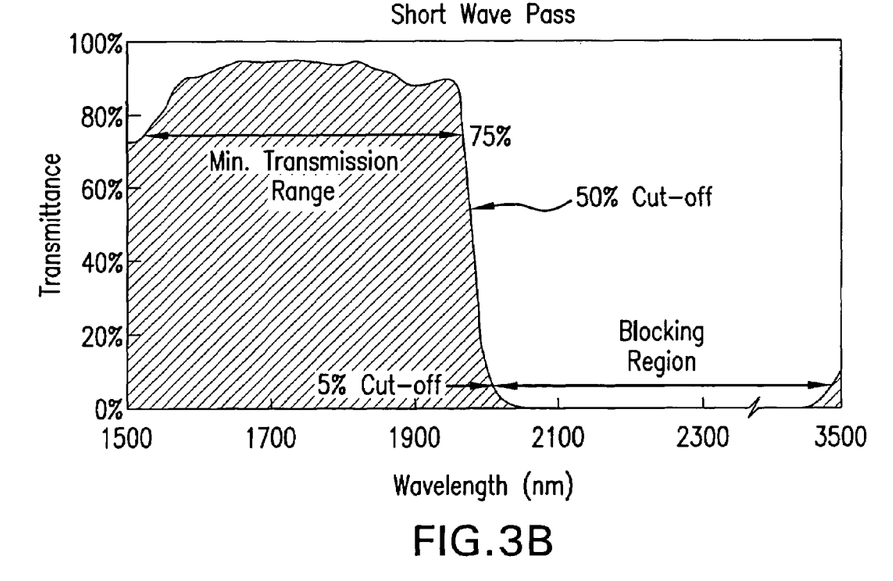

While Raman lidars have been used in measuring atmospheric constituents at kilometer distances, its ability to accurately and precisely measure airborne chemical species at shorter ranges is yet under development. Mini-Raman lidars, particularly suited to analysis from several hundred feet or less, have been only recently developed and have an upper sensitivity limit of approximately 2 g/m$^2$ from a detection range of over 500 m as against a desired level of 0.5 gm/m$^2$ for military and forensic applications. The applicant, however, recognized that Raman-lidars suffer from spectral overlapping of Raman bands. Thus, Raman signatures are often obliterated by stronger fluorescence flares from attendant specimens. Some compensation could be achieved by using lower wavelength UV laser sources (248 and 266 nm) and providing a sharp cut edge filter placed between the receiver telescope and the spectrometer to reject the strong elastically scattered laser light. The rejection ratio is typically $10^5:1$ The edge filter of the embodiments of the invention could be of long or short wave pass types produced by established multi-layer thin film coating techniques from all-dielectric materials. This manufacturing method allows a high degree of flexibility in edge position coupled with low absorption losses to be achieved, compared with bulk glass or dye filter types. Edges for long and short wave pass types can be set anywhere in the 400 nm to 5000 nm wavelength range. The filter wavelength, regardless of type, is generally specified as the 5% transmission point as shown in FIG. 3. Tolerances on this position are generally held to better than +/−2% of cut-on/off wavelength (which are defined at the 5% transmission), although this may be improved by selection. In a long wave pass type edge filter, light of lower wavelength is blocked while light of higher wavelength is transmitted through the edge filter. In a short wave pass type edge filter, light of higher wavelength is blocked while light of lower wavelength is transmitted through the edge filter. The rate of change of transmission of the edge could be approximately 5%. This is generally sufficient for most applications, although steeper edges, tending towards 2% or less, can be produced and may be preferable. Suppression of unwanted transmission 'leaks' outside the pass band could be generally better than <0.1% for the edge filters of the embodiments of the invention. Rejection levels of 0.01% or more can be achieved by the embodiments of the invention. This level of blocking performance, coupled with high average transmissions, could ensure excellent system signal to noise ratios.

A wide range of substrate materials and sizes could be used for the substrate of the edge filter. Some possible sizes of the edge filter include as 12.5 mm, 22 mm and 25 mm diameter. The edge filter can generally be operated in a temperature range is −50° C. to 100° C.

To overcome the above mentioned deficiency in Raman lidar, the embodiments of this invention uses an optical interferometry interface between the telescope and the analyzer, preferably between the telescope and the spectrometer, so as to achieve manifold enhancement in collected Raman data. Since the number density of characteristic Raman signatures has a direct dependence on detection sensitivity, even small enhancements in collection and analysis efficiency are statistically and experimentally significant. The embodiments of the invention enable a chemical distinction between red phosphorus and yellow phosphorus (explosive) and between allotropes. In one aspect of the present invention, the Raman data is conveyed and interpreted using polarization division multiplexing protocols so as to obtain unique and non-overlapping Raman signatures even in high resolution.

One embodiment of the sensor provides an optical interferometry based Raman lidar in which characteristic and fine spectrum (compared to infra-red) Raman signatures are collected, while overlapping Raman bands, if any, are resolved and differentiated using Mach-Zehnder (and other) interferometry techniques and polarization division multiplexing protocols for data transfer to a networked web of sensors. Such an embodiment allows for remote identification of chemical species without suffering from the deficiency of Raman-lidar mentioned above in its measurement or response. The embodiments of the invention can distinguish material allotropes and polymorphs. The sensitivity and analytical power of a Raman (and Brillouin) lidar is hence magnified manifold and, a desired detection limit of less than 0.1 gm/m² at range of 3.5 m could be achievable. The embodiments of the invention also provide contactless chemical identification of materials placed in transparent containers, without opening the container (i.e. vials, specimen bottles etc.).

The embodiments of the invention could use the polarization data collected from the specimen. The Raman (and Brillouin) signal received at the telescope could be passed through a beam-splitter and conveyed to the analyzer through a Sagnac or Mach-Zehnder interferometry processes that establish a calibratable phase lag between the split beams. In one embodiment of the invention, polarization multiplexing is provided to enhance Raman (and Brillouin) analysis. The split beams are combined at or prior to the analyzer (Raman spectroscope or Brillouin analyzer). Since the phase difference is known, signal resolution can provide information on spectrally overlapping Raman bands from chemical polarization data that distinguishes material allotropes and polymorphs.

The applicant also recognized that Brillouin scattering techniques could have an advantage in comparison with Raman scattering because the narrow Brillouin line width could maximize the effects of daylight and fluorescence. Thus, one embodiment of the invention provides an interferometry interface between the telescope and the analyzer, preferably between the telescope and the spectrometer, so as to achieve manifold enhancement in collected Brillouin data. In embodiments of the invention, the Brillouin data could be conveyed and interpreted using polarization division multiplexing protocols so as to obtain unique and non-overlapping characteristic Brillouin signatures of chemical identity, temperature or location.

As an analytical technique, Raman spectroscopy has major advantages, the most important being the ease of sample preparation and the rich information content. Raman is essentially a light scattering technique, so all that is required for collection of a spectrum is a means to place the sample into the excitation beam and collecting the scattered light. Therefore in the embodiments of the invention, there are few concerns with sample thickness (as in transmission analyses) and little contribution from the ambient atmosphere, so there is no need for high-vacuum or desiccated sample holders. Glass, water and plastic packaging each have very weak Raman spectra, making the technique easy to use. Often, samples of the embodiments of the invention can be evaluated directly inside the glass bottle or plastic bag without opening the package and risking contamination. Advantageously over infrared spectroscopy, aqueous samples are readily evaluated without the need to remove water, and because ambient humidity is not a problem, there is no need to purge the instrument.

No two molecules would give exactly the same Raman spectrum, and the intensity of the scattered light is related to the amount of material present. This makes it easy to obtain both qualitative and quantitative information about the sample, allowing for spectral interpretation, library searching, data manipulations and the application of quantitative analysis computer methods. However, certain molecular combinations may yield spectrally overlapped Raman bands and make species identification somewhat difficult for allotropes and polymorphs. Besides, Raman scattering, being an indicator of fine vibrations and structure, is easily obliterated or smothered by stronger fluorescence signals emitted under the same excitation. These deficiencies have been discussed above.

Raman spectroscopy by the embodiment of this invention is generally non-destructive. Unlike IR—or other spectroscopy techniques, there could be no need to dissolve solids, press pellets, compress the sample against optical elements or otherwise alter the structure of the sample in the embodiments of the invention. Raman spectrometers of the embodiments of the invention could employ one of two technologies for the collection of spectra: (1) Dispersive Raman spectroscopy and (2) Fourier transform Raman spectroscopy. Each technique has its unique advantages and is suited to specific analyses. Raman spectroscopy may also be performed on chemical species in the vapor phase without having to chemically fix the species. Some embodiments of the invention also include microscopic examination of the samples using Raman microscopes and Raman confocal microscopes to analyze for texture.

In order to identify chemical species in a sample, it is desirable to establish a library of Raman spectra for the chemical species in the sample and the container. This library should preferably be quickly searched for matches with the measured spectra. In the embodiments of the invention, an adaptive mixing algorithm could be used to simultaneously determine the mixing coefficients of many chemical species, e.g., 12 chemical species, in a simulated composite spectrum. In some embodiments of the invention, spectral database could contain signatures of hundreds of disguising chemical species designed to disguise identification of potentially harmful chemical species. The disguising effect could be either via the use of chemical mutants or fluorescing fillers that fluoresce within the Raman spectral window. This problem of disguising a harmful chemical species could be particularly acute because fluorescence in some degree is always present in nearly all samples. Such population may lower the confidence level in data at the desired detection limit of 0.5 $g/m^2$.

The embodiments of the invention could use dispersive Raman, usually employing visible laser radiation. The laser wavelengths could be 780 nm, 633 nm, 532 nm, and 473 nm, although others are common. Since the efficiency of Raman scatter is proportional to $1/\lambda^4$, there is a strong enhancement as the excitation laser wavelength becomes shorter. Such feature is particularly useful in Raman based lidars, wherein 266 nm and 248 nm laser sources are preferably used.

Figure 4:
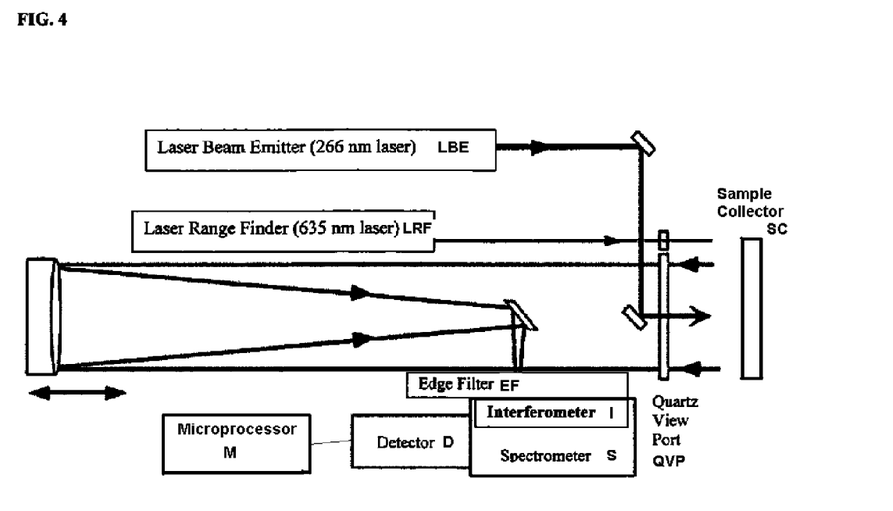
FIG. 4 shows an embodiment of the Raman lidar based optical sensor.

A Raman lidar of the embodiments of the invention functions somewhat like a Raman spectroscope with the exception that the light source is usually comprises a UV-laser. As an example, the optical path of the light beam to and from the specimen is represented in FIG. 4. The light source travels to the sample, not shown in FIG. 4, but located to the right of the sensor shown in FIG. 4, after bouncing off a mirror. Captured Raman signals are telescopically received at the 6 inch or larger mirror and focused and filtered and conveyed to a spectrometer where they are evaluated and correlated to the specimen. Better focusing may be achieved by providing motorized movement to the mirrors.

The embodiments of the invention include an interferometry interface or module as shown in FIG. 4. The interferometry module could be placed at any location between the sample and the quartz view port in FIG. 4, for example, or anywhere where the captured Raman signals from the sample passes through. In one embodiment, the interferometry module could be located at the point of entry of the captured Raman signals into the spectrometer, i.e. in FIG. 4, the interferometry module could be provided between the edge filter at one end and the spectrometer at the other end. In another embodiment, the interferometry module could be located at the point of entry of the captured Raman signals into the detector, i.e. in FIG. 4, the interferometry module could be provided between the edge filter at one end and the detector at the other end. Also, even though FIG. 4 appears to shows the captured Raman signals traversing through the edge filter into the spectrometer, with the detector attached to spectrometer, in some embodiments of the invention the captured Raman signals could traverse through the edge filter into a interferometry module, a spectrometer, a detector, which could have multiplex array Raman detectors, and to one or more analyzers for analyzing the captured Raman signals that have been phase shifted by the interferometry module to separate overlapping peaks.

FIG. 4 shows that the spectrometer is before the detector, but after the interferometer. However, the interferometer could communicate to a multiplexed array of detectors such as those shown in FIG. 5, either directly or via the spectrometer (the spectrometer also has its own detectors). The actual configuration is decided by the identity, number and distribution of the species being targeted. If one wants to closely analyze the signals in a specific band, one could detect (gather the data) first and then perform the identification/labeling.

Figure 5:
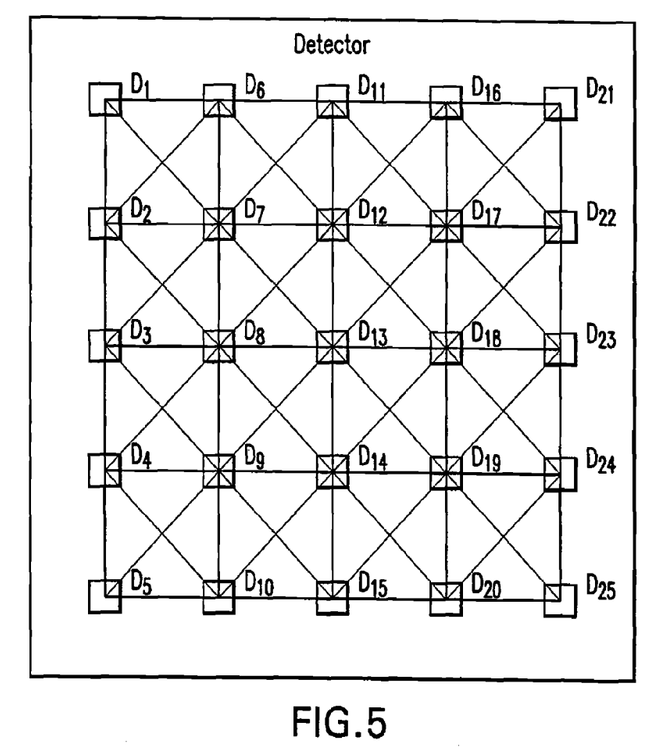
FIG. 5 shows an embodiment of an array detector.

FIG. 5 shows an example of a multiplexed array of detectors with 25 detectors, wherein each one of the detectors could be an optical or electronic detector such as photodiode detectors. The input to the array of detector of FIG. 5 is at D1 and the output is at D25, for example. The interferometer can communicate to the multiplexed array of detectors either directly or via the spectrometer. The actual configuration could be decided by the identity, number and distribution of the species being targeted. The lines in FIG. 5 indicate exchange of evaluated information between detectors that have been assigned specific Raman traffic. Spectroscopic features arising from "innocuous elements" could be subtracted from incoming signal so as to quicken the total analysis (subsequently less Raman traffic to send to the detectors).

The multiplexed array of detectors with 25 detectors could be made and operated in the embodiments of the invention as follows, for example. One should decide the wavelength and resolution limits of interest. Detectors could be arranged in specific order of their sensitivity and operating regimes with more number of detectors provided along wavelengths of interest. All detectors communicate to a microprocessor and to each other. Incoming Raman signal could arrive at the microprocessor that directs each constituent (or feature present at certain wavelength) to a detector that is particularly sensitive at that wavelength. Features at other wavelengths could be evaluated by other detectors. Irrelevant/innocuous features could be communicated to the microprocessor so as to exclude them from further analysis. When every feature of incoming signal has been evaluated and analytical stability has been established for a certain number of seconds, the multiplexing stops and the microprocessor could announce its chemical verdict.

In the embodiments of the invention, the spectrometer (which could have its own detector) could first detect a composite Raman signal spectrum. This spectrum could be analyzed by the microprocessor, which in turn can set the amount of phase shift in the interferometer and also direct each constituent (or feature present at certain wavelength), to a detector that is particularly sensitive at that wavelength. In one embodiment, the microprocessor could set the amount of phase shift in the interferometer, or the microprocessor could just direct each (or feature present at certain wavelength), to a detector that is particularly sensitive at that wavelength, or does the microprocessor do both the functions of directing each (or feature present at certain wavelength), to a detector that is particularly sensitive at that wavelength and optionally set the amount of phase shift in the interferometer. In short, in the embodiments of the invention, the microprocessor could perform both the functions of directing each (or feature present at certain wavelength), to a detector that is particularly sensitive at that wavelength and optionally set the amount of phase shift in the interferometer.

While no two materials have Raman peaks at the same wavelength, there could be disguising and disguised peaks, which means two peaks that are so close to each other that it would be hard to separate the two individual peaks as two separate peaks in a composite spectrum. In this situation, a slight phase shift between the two peaks by an interferometer can help separate the two peaks for improved identification.

This is a principle of the interferometer of the embodiments of the invention.

The interferometer of the embodiments of the invention could be an optical device that splits a wave into two or more waves, using a beam splitter, delays them by unequal distances, redirects them using mirrors, recombines them using another (or the same) beam splitter, and detects the intensity of their superposition. Depending on variations and detail in design and function, interferometers of the embodiments of the invention could be of many kinds including Mach-Zehnder, Michelson, Sagnac, Fabry-Perot, Murty and the like.

The interferometry module could also be a microprocessor (rather than an optical device) that that functions similarly to an optical device such that it splits a wave, particularly which has been digitized electronically, into two or more waves. Also, the captured Raman signals could be conveyed by an optical fiber to the spectrometer, which could be separated from the rest of the sensor shown in FIG. 4, such that the sensor could be miniaturized and used for medical diagnostics such as colonoscopy.

In one embodiment, a Mach-Zehnder interferometer could be of particular interest due to its narrow-band wavelength capabilities that make it particularly suited for electric field sensing and similar capabilities. A Mach-Zehnder interferometer (referred to hereinafter as MZI) is an apparatus having at least one optical input, two interferometer arms, at least one optical output and two optical couplings, capable of working as optical power splitters, one between the at least one input and the interferometer arms, the other between the interferometer arms and the at least one output.

MZIs of the embodiments of the invention are particularly attractive in several applications, both in the field of telecommunication and in the field of sensors. MZIs allow, for example to vary the optical power splitting ratio on their outputs in dependence of a difference in optical length of the two interferometer arms. A difference in optical length between the two arms can be deliberately induced, for example by means of a suitable control, to obtain a variable attenuator or an optical switch. Otherwise, this effect can be exploited to detect or measure characteristic properties of materials or structures which, once inserted in one of the two interferometer arms, can induce variations in the optical length thereof.

Particularly for fine detection, the fiber optic sensor preferably is the MZI sensor. In an embodiment of the interferometry sensor, the phase modulation is mapped as an intensity modulation through a raised cosine function. Because of the nonlinear transfer function, a sinusoidal phase modulation generates higher order harmonics. An interferometer biased at quadrature (interfering beams $\pi/2$ out of phase) has a maximum response at the first order harmonic and a minimum response at the second order harmonic. For this reason, quadrature is the preferred bias point. As the bias point drifts away from quadrature (for example, due to external temperature changes or, in the case of Raman lidars due to change in chemical composition), the response at the first order harmonic decreases and the response at the second order harmonic increases. When the interferometer is biased at 0 or $\pi$ out of phase, the first order harmonic disappears completely. The decreased response at the first order harmonic (resulting from the bias points away from quadrature) is referred to as signal fading.

Because MZI sensors have an unstable bias point, they are especially sensitive to the signal attenuation (or drift) as mentioned. In order to overcome signal fading, a demodulation of the returned signal is preferred. The typical demodulation technique could be the Phase-Generated Carrier (PGC) scheme, which requires a path-mismatched MZI sensor. The path imbalance also causes the conversion of laser phase noise into intensity noise which particularly qualifies the performance of an MZI sensor array at low frequencies and places stringent requirements on the linewidth of the source in the wavelength regime of about 1550 nm.

In the embodiments of the present invention, an MZI array is particularly suited to Raman lidars based on low wavelength laser sources. Typical MZIs could have two inputs and two outputs and are represented as "2×2 MZI", although simpler MZIs can have only one input and one output. A 2×2 MZI using single-mode optical guides comprises a first pair of optical guides and a second pair of optical guides. The optical guides (or waveguides) can be optical fibers or integrated guides, which are bi-directional or reciprocal: the first pair of optical guides and the second pair of optical guides can be used alternately as inputs, respectively outputs, or as outputs, respectively inputs, and the operation being nominally identical in the two cases.

The first pair of optical guides and the second pair of optical guides are coupled to respective optical couplings, acting as optical power splitters. The two optical couplings are coupled to each other by means of two optical guide segments, forming the interferometer arms.

Each of the interferometer arms could have an optical length equal to $\beta L$, where $\beta$ is the propagation constant of the propagating mode and L is the physical length of the arm. The propagation constant $\beta$ is in turn equal to $(2\pi/\lambda)*n$, where $\lambda$ is the wavelength of the propagating mode and n is the refractive index of the propagating mode. The two arms can have equal or different optical lengths: in the former case the interferometer is said to be balanced, while in the latter it is said to be unbalanced.

Typically, each optical power splitter splits into two nominally equal parts the optical power received on either one of the two inputs thereof. More generally, the optical splitting ratios of the two optical power splitters can be different from 50%, and also be different from each other.

By properly designing the electrical power splitting ratios of the two optical power splitters and the degree of unbalance of the interferometer arms, it is at least nominally possible to obtain on the outputs, by interferometric effect, any optical power splitting ratio from 0% to 100% of the optical power supplied to the optical power splitter through any one of the two inputs, independently of the operating optical band of the optical power splitters.

In particular, for optical power splitters having a 50% splitting ratio (also referred to as 3 dB optical power splitters) on a nominally infinite optical band (in practice, on the whole band of the single-mode optical guides), a balanced MZI is capable of transferring on one of the two outputs thereof the whole optical power received through one of the two inputs thereof, on a nominally infinite optical band. In the same condition, an unbalanced MZI in which the difference between the arm optical lengths is equal to $\pi$ at a predetermined wavelength is capable of transferring the whole optical power from one input to one output thereof only at the predetermined wavelength.

In a MZI having only one input and one output, the unbalance between the two arms only determines an output attenuation of optical power. MZIs are widely used in many applications in optics, largely due to the structural simplicity thereof and because they are formed by elements that can easily be practically implemented in optical guides, such as integrated waveguides or optical fibers, exploiting a single technology.

In some embodiments of the invention, the MZI configuration for miniaturization could use folded MZI sensors. Folded MZI sensors, often made using flexible materials, occupy less space and also permit the layout of input and output channels on the same side of MZI, making them particularly suitable for microelectronic and MEMS based sensing and signal conveying applications.

In some embodiments of the invention, there could be a multiplex array of detectors and multiplexing of Raman signals. In the embodiments of the present, multiplexing is defined as the combination of several Raman (or Brillouin) signals for transmission of the plurality of Raman signals through a shared medium or waveguide. The Raman signals are combined at the input transmitter by a multiplexer and split up at the receiver by a demultiplexer.

The multiplexing protocols for collection of Raman signals could include data travel along an optical path in a variety of ways including time division multiplexing (TDM), wavelength division multiplexing (WDM), code division multiplexing, polarization division multiplexing and other means.

Time division multiplexing (TDM) is one method of putting multiple data streams in a single input signal by separating the signal into many segments, each having a very short duration. Each individual data stream is reassembled at the output end based on the timing. The circuit that combines signals at the source (transmitting) end of a communications link is known as a multiplexer. It accepts the input from each individual end user, breaks each signal into segments, and assigns the segments to the composite signal in a rotating, repeating sequence. The composite signal thus contains data from multiple senders. At the output end of the cable, the individual signals are separated out by means of a circuit called a demultiplexer, and routed to the proper end users. A two-way communications circuit requires a multiplexer-demultiplexer at each end of the long-distance, high-bandwidth cable. If many Raman signals must be sent along a single line, careful engineering is required to ensure that the system will perform properly. An asset of TDM is its flexibility. The scheme allows for variation in the number of signals being sent along the line, and constantly adjusts the time intervals to make optimum use of the available bandwidth. The internet is an exemplary instance of a communications network in which the volume of traffic can change drastically from hour to hour. In some systems, a different scheme, known as wavelength division multiplexing (WDM), is preferred wherein the deriving of two or more channels from a transmission medium occurs by assigning a separate portion of the available frequency (or wavelength) spectrum to each of the individual channels. Wavelength division multiplexing (or frequency division multiplexing) is generally popular with telecommunication companies because it allows them to expand the capacity of their fiber networks without digging up the road and simply upgrading the multiplexer-demultiplexer at the input and output ends of the cable. Another form of multiplexing: code division multiplexing (or Code Division Multiple Access—CDMA) is when an input transmitter encodes the input signal using a pseudo-random sequence which the output receiver also knows and can use to decode the received signal. Each different random sequence corresponds to a different communication channel. CDMA is extensively used for digital cellular phones and in the transmission of voice messages through telephone and computer networks. In a preferred embodiment of the present invention, polarization multiplexing protocols provide unique and non-overlapping Raman (or Brillouin) interpretation.

Fabricating a Sensor with an Interferometer

The method of manufacturing a sensor comprises locating a beam emitter that emits a first beam comprising laser, a beam-splitting interferometer and a detector within the sensor in a manner such that the first beam strikes a sample and produces a second beam comprising a Raman signal, and the beam-splitting interferometer creates a phase delay in the second beam.

The beam-splitting interferometer could be MZIs, which can be practically fabricated by means of three main technologies. A first technology makes use of planar technology applied to substrate materials such as lithium niobate, semiconductor materials, silica glass, with integrated planar optical guides. A second technology, also referred to as all-fiber technology, allows fabricating MZIs directly from two optical fibers, properly coupled to each other to form the optical power splitters. A third technology allows fabricating MZIs on a single wafer wherein the optical structures are developed and interfaced using standard etching, photomasking and photolithography procedures and MZI is interfaced with a devise using contact metal pads, in-situ cast nanowires, conducting polymers, and combinations thereof.

In one embodiment, the Mach-Zehnder structure is formed by at least one of lithography, photolithography, photomasking, photopatterning, micropatterning, sputtering, or a combination thereof. In another embodiment, the formed Mach-Zehnder structure is cut using a diamond saw along a predetermined cutting axis. In yet another embodiment, the metallic layer is formed using at least one of sputtering, evaporation, physical vapor deposition, chemical vapor deposition, or a combination thereof and comprises at least one of gold, silver, nickel, titanium, titanium-tungsten, copper, aluminum, platinum, silica, tantalum, tantalum nitride, chromium, or a combination thereof. In one embodiment, the folded Mach-Zehnder interferometer is patterned on a single wafer.

Operation of the Sensor with the Interferometer

The sensor employs Raman spectroscopy wherein a beam is directed toward a target (i.e., a sample) in order to determine its composition. The target is illuminated by the beam and the resulting scattered light energy is collected. The collected in elastically scattered light is spectrally resolved and the wavelength shift of the scattered laser light with respect to the incident laser light is detected. The particular shift, or set of shifts, provides a unique fingerprint of the substance which is being interrogated, thereby permitting personnel to determine the agent's composition.

Now refer to FIG. 4, which is a schematic illustration of the mini-lidar sensor of the present invention. The sensor generally preferably includes a beam transmitter for transmitting a laser beam to a sample (which is not shown in FIG. 4), an optical view port through which the Raman signal enters the sensor, internal mirrors, lenses and prisms to direct the Raman signal from the view port to an edge filter shown in FIG. 4, an interferometer, a spectrometer, a detector, and optionally a beam alignment device (not shown in FIG. 4) to align the laser beam. Each of these components may be compactly configured on a support platform.

The beam alignment device could structurally fix the laser beam emitter proximal to the optical detector (telescope) that contains the view port and optics, to effect the alignment of the laser beam and achieve a desired transmission path. A structural connection between the laser beam emitter and optical detector may include a mounting bracket (not shown in FIG. 4) between the laser beam emitter and the optical detector.

In the present invention, when laser beam strikes the surface of a sample which is to be interrogated, laser light is scattered and reflected back toward the view port of the telescope shown in FIG. 4. The view port collects the scattered photons in the light energy arriving at the view port and optics within the telescope concentrates the light energy which is emitted from telescope output end to the edge filter shown in FIG. 4. As set forth above, the scattered light is both elastic and inelastic in nature with the elastic scatter dominating. The strength of the strong elastically scattered return compared to the faint inelastic Raman scatter, which is used to determine the composition of the target, could be beyond the dynamic range of commercially available optical array detectors. Elastically scattered light is preferably rejected by use of filtering device such as an optical filter such as an edge filter positioned directly adjacent telescope output end. The filtering device is to permit the transmission of inelastic scattering component of the beam coming from the output of the telescope and to substantially reject the elastic scattering component, so that it may be processed to determine target composition. In an alternative embodiment, filtering device may include a single stage grating spectrometer which acts as a predisperser for rejecting the elastically scattered light. The predisperser rejects the elastically scattered light and permits the passage of inelastically scattered light, which is employed in Raman spectroscopy.

Figure 6:
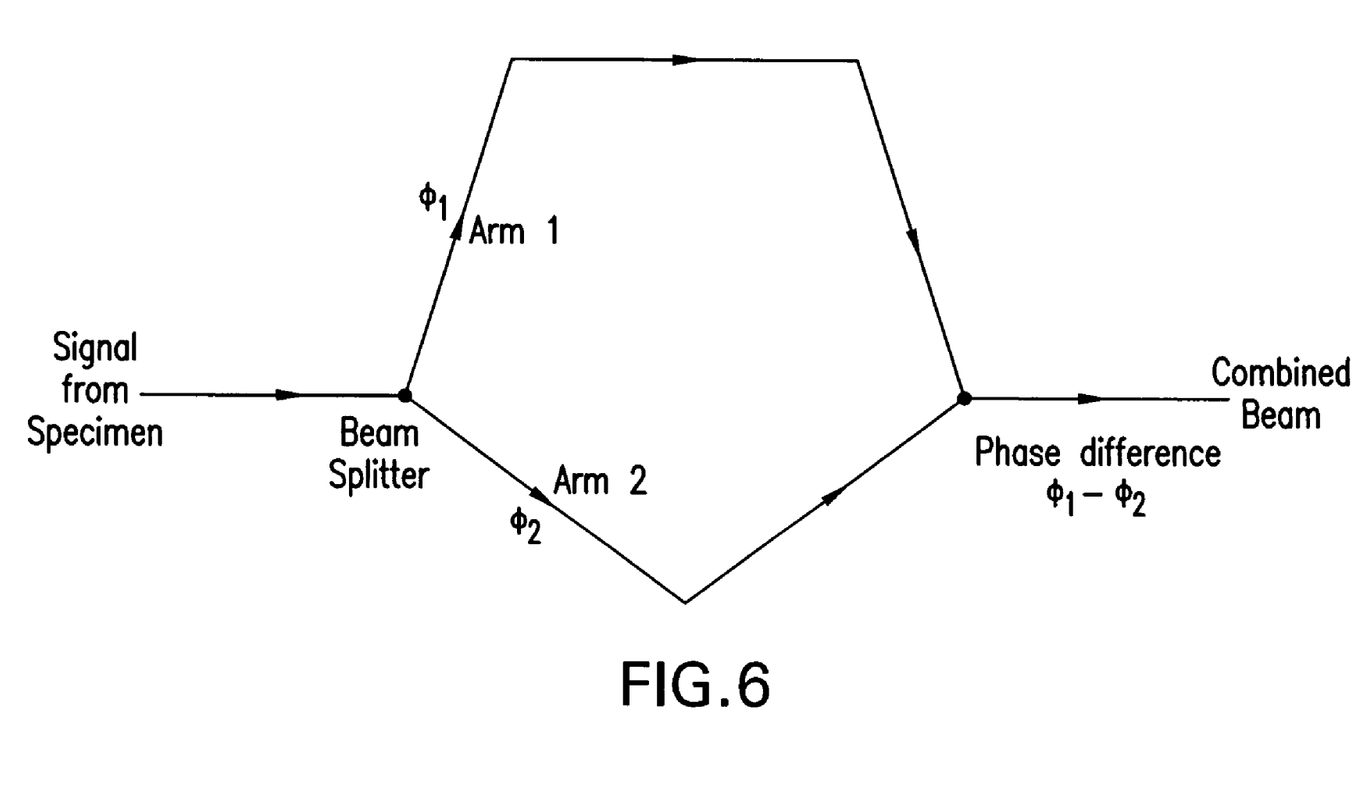
FIG. 6 shows the mechanism of beam splitting by a beam-splitting interferometer.
Figure 7:
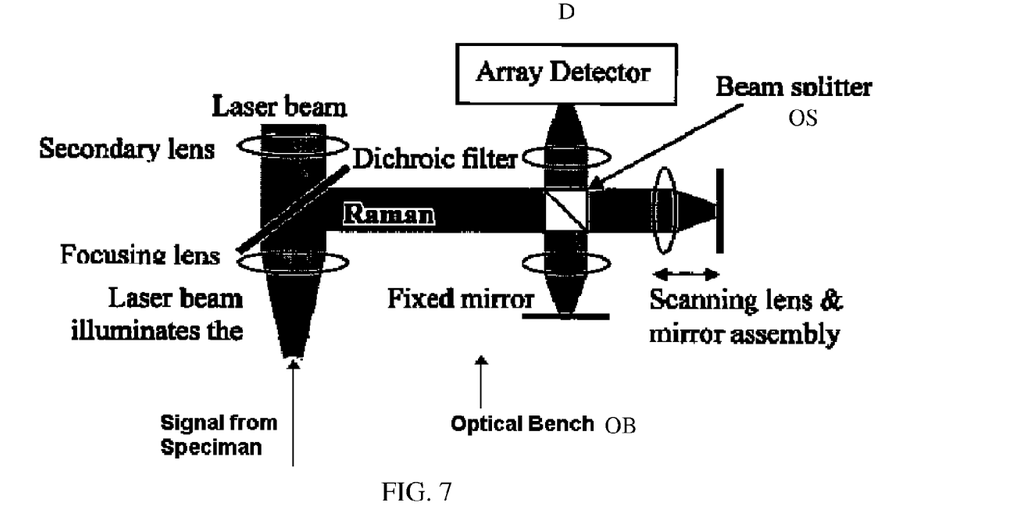
FIG. 7 is a schematic diagram illustrating an embodiment of the invention.
Figure 8:
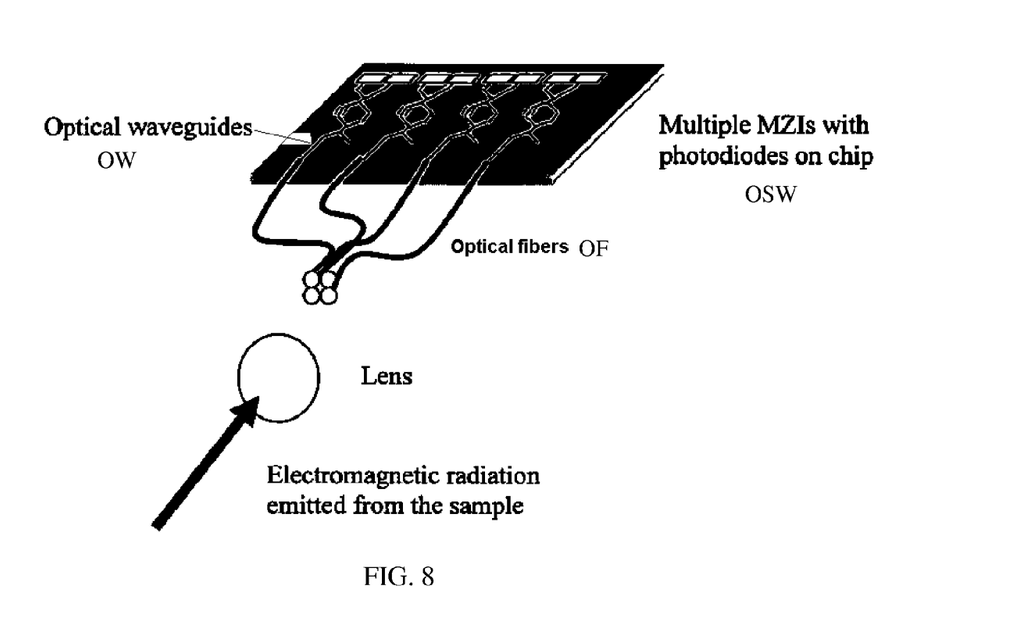
FIG. 8 is a schematic diagram illustrating an embodiment of the invention.

The light energy transmitted through the filtering device is then processed by an interferometer. The interferometer splits the incoming beam to the interferometer and creates a phase delay between the two split beams by changing the path length difference as shown in FIG. 6. The one embodiment of the interferometer, a variable index-of-refraction material is put in one of the two beam paths. By carefully controlling the index-of-refraction of the material, different interference fringe are formed. The two beams are again combined into one beam that exits the interferometer into a spectrum resolving device such as a spectrometer. A variety of spectrometers may be employed. The light energy enters an input slit of spectrometer which is adjacently disposed to the spectrometer, and is resolved into its various component wavelengths forming a spectra. The output of the spectrometer is bands of faint light which contain the information which can be evaluated to determine the composition of the target.

In order to convert the optical information into electronic signals for processing, the sensor further includes one or more detectors (array detector), as shown in FIG. 5, for example, which could detector transducers or photodiodes. The detector transducer could be an intensified charged couple device, ICCD, which has a high degree of sensitivity to light. The ICCD converts the light energy into electronic signals which may then be processed by a computer device such as a microprocessor. Alternatively, a low noise CCD detector may be employed. The telescope, edge filter, spectrometer and an array detector are all aligned in way, for example as shown in FIG. 4, resulting in a compact design.

The information received by the detector is then preferably fed to a micro computer where the information is processed in order to indicate to the users the composition of the target agents being interrogated. The information collected by the sensor can then be outputted in the form of a graph or in any other suitable readable form on a computer terminal, paper or any form of storage medium.

If the output is plotted as a graph, then the Raman return intensity forms the Y axis which is the sum of light signals falling onto a particular vertically aligned column of pixels of the array detector. The shift of Raman lines with respect to the laser excitation could form the X axis. The Raman shift is labeled in frequency units known as wavenumbers, or inverse centimeters ($cm^{-1}$), wherein the conversion between wavelength and wavenumbers is an inverse relationship. Each Raman-activated molecule has its own unique Raman fingerprint; therefore, the information collected can be compared either manually or via a micro processor to the data of known compounds such that the sensor can accurately determine the composition of the substance that is being interrogated. For example, a micro processor, such as a portable laptop computer could be programmed to interpret the output of the array detector and display the chemical or biological composition and concentration of the target substance. The displayed information would be easily comprehended by an emergency worker, with little or no scientific background. Based on the results of the scan, appropriate measures could be taken to contain the contamination and insolate the affected area. The various components of the sensor could be securely mounted to a rigid platform, attached to any piece of equipment such as a sensor holder attached to a wall, for example, or could be integrated within a hand-held sensor unit.

In the embodiments of this invention, the method and/or analysis of collection of the Raman signal from a sample could depend on the type of the sample. For example, if the sample is liquid or solid on a surface, then the surface could act as the background against which the Raman signal from the liquid or solid could be compared to provide an analysis of the liquid or solid in about 60 seconds. If the sample is a particulate solid, liquid or a gas/vapor floating in space such as air, then there could be no background against which to compare the Raman signal from the sample can be compared. In this case, the electromagnetic beam comprising laser striking the sample may need to strike the sample repeatedly in the space having three-dimension where the sample is located. Then, the analysis of the sample would be over the three-dimensions of the sample, resulting in a longer analysis time, i.e., about 180 second, as compared to the analysis time for a liquid or solid sample on a surface.

The embodiments of the invention could further include a sample collection device for collecting the sample that has to be evaluated by the sensor of the embodiments of the invention. The sample collection device could include a suction and sample concentration devices. For example, a solid, liquid or gaseous sample could be sucked into a sample collection device that produces a known background signal. Then, the sample could be concentrated within the sample collection device. For example, a gas could be cooled to create condensate in the sample collection device. By concentrating the sample in the sample collection device, it could reduce the analysis time, particularly for a gaseous sample.

While only certain features of the invention have been illustrated and described herein, many modifications and changes will occur to those skilled in the art. It is, therefore, to be understood that the appended claims are intended to cover all such modifications and changes as fall within the true spirit of the invention.

The sensor could also be used for therapeutic materials development, i.e., for drug development and for biomaterial studies, as well as for biomedical research, analytical chemistry, high throughput compound screening, and bioprocess monitoring. Yet another applications of the sensor could be for developing new materials, particularly nanomaterials for many purposes including, but not limited to corrosion resistance, battery energy storage, electroplating, low voltage phosphorescence, bone graft compatibility, resisting fouling by marine organisms, superconductivity, epitaxial lattice matching, or chemical catalysis.

It is further contemplated that sensor of the embodiments of the invention could be used to develop screening methods for testing materials. That is, reagents electrochemically generated by an electrode on a die could be used to test the physical and chemical properties of materials. For example, the sensor could be used for testing corrosion resistance, electroplating efficiency, chemical kinetics, superconductivity, electro-chemiluminescence and catalyst lifetimes.

The embodiments of this invention have yet other several practical uses. For example, one embodiment of the invention allows molecules and nanomaterials detection/analysis based on the electrical readout of specific captured Raman signals (fingerprints) of molecules and nanomaterials. Another embodiment of the invention has potential applications for nanomaterials study to be used in electronic devices (transistors and interconnects) as well as well as for detection of bio-species (DNA, protein, viruses etc.) for molecular diagnostics, homeland security, drug discovery and life science R&D work.

This application discloses several numerical range limitations that support any range within the disclosed numerical ranges even though a precise range limitation is not stated verbatim in the specification because the embodiments of the invention could be practiced throughout the disclosed numerical ranges. Finally, the entire disclosure of the patents and publications referred in this application, if any, are hereby incorporated herein in entirety by reference.

The invention claimed is:

1. A sensor comprising:
   a beam emitter that emits a first beam with a laser,
   a beam-splitting interferometer, and
   a spectrometer and an array detector comprising a multiplexed array of detectors
   wherein the detectors have different sensitivity and are arranged in order of their sensitivity and/or operating regimes,
   wherein the first beam is to strike a sample that produces a second beam comprising a Raman signal, said beam-splitting interferometer creates a phase delay in the second beam,
   wherein said phase delay provides information on overlapping Raman signals.

2. The sensor of claim 1, further comprising optical elements to collect the second beam and concentrate the second beam.

3. The sensor of claim 1, further comprising an edge filter.

4. The sensor of claim 1, wherein the spectrometer comprises diffraction gratings.

5. The sensor of claim 1, further comprising a microprocessor.

6. The sensor of claim 5, wherein the microprocessor performs computational functions on a library of Raman spectra.

7. The sensor of claim 1, wherein the array detector comprises a detector which is a charge coupled device, a transducer or a photodiode.

8. The sensor of claim 1, wherein the interferometer comprises an optical bench, a wafer having optical structures, an optical splitter or an optical waveguide.

9. The sensor of claim 8, wherein the optical splitter or the optical waveguide comprises optical fibers coupled to each other to form the optical splitter or the optical guide.

10. A method for spectroscopic detection of a sample, comprising generating a first beam comprising laser, striking the first beam to a sample to produce a second beam comprising a Raman signal, creating a phase delay in the second beam with a beam-splitting interferometer, passing the second beam through a spectrometer, spreading the Raman signal onto a multiplexed array of detectors that have different sensitivity and are arranged in order of their sensitivity and/or operating regimes and detecting the Raman signal of the second beam.

11. The method of claim 10, further comprising permitting transmission of the Raman signal of the second beam through a filtering device that substantially rejects non-Raman signals of the second beam.

12. The method of claim 10, wherein the second beam is modified to substantially exclude all IR signals and include substantially only the Raman signal.

13. The method of claim 10, wherein the multiplxed array of detectors has a sensitivity to resolve overlapping Raman signals having a Raman scattering cross-section as low as about $10^{-29}$ cm$^2$/molecule.

14. The method of claim 13, further comprising analyzing an output of the array detector.

15. The method of claim 14, further comprising comparing Raman spectra stored in a library to a Raman spectrum from an output of the array detector.

16. The method of claim 10, wherein the sample is at a distance of greater than 30 meters from the array detector.

17. A method of manufacturing a sensor, comprising providing
   (a) a beam emitter that emits a first beam with a laser,
   (b) a beam-splitting interferometer,
   (c) a spectrometer and
   (d) a multiplexed array of detectors,
   the detectors having different sensitivity and arranged in order of their sensitivity and/or operating regimes within the sensor in a manner such that the first beam strikes a sample and produces a second beam comprising a Raman signal, the beam-splitting interferometer creates a phase delay in the second beam, and the second beam passes through a spectrometer to the multiplexed array of detectors.

18. The sensor of claim 1, wherein the array of detectors has more detectors provided along wavelengths of interest.

* * * * *